United States Patent [19]

Juhl et al.

[11] Patent Number: 4,605,801
[45] Date of Patent: Aug. 12, 1986

[54] MOLECULAR SIEVES AS CATALYSTS FOR PREPARATION OF 1,1,2-TRICHLOROETHANE

[75] Inventors: Roger L. Juhl; Mark S. Johnson; Thomas E. Morris, all of Lake Jackson, Tex.

[73] Assignee: The Dow Chemical Company, Midland, Mich.

[21] Appl. No.: 437,711

[22] Filed: Oct. 29, 1982

[51] Int. Cl.$^4$ ............................................. C07C 17/10
[52] U.S. Cl. ..................................... 570/253; 570/255
[58] Field of Search ............................. 570/255, 253

[56] References Cited

U.S. PATENT DOCUMENTS

| 2,998,459 | 8/1961 | Baker et al. ....................... 570/254 |
| 3,130,007 | 4/1964 | Breck ................................. 23/113 |

FOREIGN PATENT DOCUMENTS

| 240155 | 8/1962 | Australia ........................... 570/255 |
| 344592 | 3/1931 | United Kingdom ............... 570/253 |

Primary Examiner—Charles F. Warren
Assistant Examiner—Joseph A. Boska
Attorney, Agent, or Firm—A. C. Ancona

[57] ABSTRACT

The process is an improvement over the chlorination of EDC in a boiling bed. The reactants, chlorine and dichloroethane (either 1,1- or 1,2-) are mixed in the vapor phase and passed over a molecular sieve which serves as a catalyst to produce 1,1,2-trichloroethane.

6 Claims, No Drawings

MOLECULAR SIEVES AS CATALYSTS FOR PREPARATION OF 1,1,2-TRICHLOROETHANE

BACKGROUND OF THE INVENTION

It is well known to make 1,1,2-trichloroethane (β-trichloroethane) by chlorinating 1,2-dichloroethane (ethylene dichloride) in a boiling bed reactor. Conversion of the ethylene dichloride (EDC) is generally about 22% per pass with a 75% conversion for chlorine. The reaction is a substitution reaction wherein HCl is formed as a by-product.

The present process, in contrast, is a vapor phase reaction which provides 100% conversion of chlorine per pass and 30 to 50% or better conversion of EDC per pass.

SUMMARY OF THE INVENTION

The process is an improvement over the chlorination of EDC in a boiling bed. The reactants, chlorine and dichloroethane (either 1,1- or 1,2-) or mixed in the vapor phase and passed over a molecular sieve which serves as a catalyst to produce 1,1,2-trichloroethane.

DETAILED DESCRIPTION OF THE INVENTION

The dichloroethane, which may be either the 1,1-di- or the 1,2-di-isomer, is vaporized and mixed with chlorine vapor prior to passing over the molecular sieve which is employed as the catalyst. The catalyst is preferably a molecular sieve of the Y-type structure. The $SiO_2/Al_2O_3$ molecular ratio of 3-6 is typical for this type structure.

The temperature of reaction is generally from about 100° to about 350° C. and preferably from about 110° to about 200° C. Temperatures above about 350° C. produce carbonaceous residues and with those below 100° C. the organic reactant and or by-products accumulate on the surface of the catalyst, blocking access to the reactive sites on the molecular sieve and reducing its effectiveness.

Residence time can be from about 0.1 to 30 seconds, depending upon the temperature. The preferred range is from about 1 to about 3 seconds.

Pressures of from about atmospheric up to about 25 atmospheres are useful. Higher pressures would promote accumulation of organic reactant on the surface of the molecular sieve. Less than atmospheric would reduce efficiency.

Molar ratios of chlorine to dichloroethane from about 1:1 to about 1:10 can be employed. Greater than 1:1 will cause production of the higher chlorinated products, ie tetra-, penta- and hexachloroethanes. Lower than 1:10, while resulting in higher yields of the desired product, would produce higher amounts of recycled dichloroethane.

The following experiments are illustrative of the invention:

EXAMPLE 1

A simple one-pass vapor-phase reactor was used. The reactor was a Pyrex (1.31 by 0.059 ft) tube having a volume of 6.22 in$^3$ (0.00358 ft.$^3$). Chlorine and 1,1-dichloroethane flow rates were regulated by needle valves and measured by calibrated rotameters. A helium gas pad was used to eliminate the presence of oxygen and nitrogen. The 1,1-dichloroethane was vaporized and mixed with chlorine in a static mixer. The mixture then passed through the reactor containing 61.5 g of ⅜" extrudate type-Y molecular sieve, available commercially as Linde* LZY-52 molecular sieve. The effluent was then purged into a caustic solution. Samples for analysis were obtained in a chilled potassium iodide solution. The temperatures, feed rates, flow rates, conversions, and selectivities are listed in Table I for four runs.

*Trademark of The Union Carbide Company

TABLE I

| Run No. | 1 | 2 | 3 | 4 |
|---|---|---|---|---|
| Temp. (°C.) | 110 | 165 | 200 | 200 |
| $R_T$ (Sec.)* | 2.1 | 1.6 | 1.4 | 1.1 |
| 1,1-Di/Cl$_2$ Mole Feed Ratio | 3.5 | 2.0 | 2.0 | 3.9 |
| Cl$_2$ Conversion (%) | 100 | 100 | 100 | 100 |
| 1,1-Di Conversion (%) | 33 | 45 | 58 | 44 |
| 1,1-Di (Mol %) | (Product selectivity from the converted 1,1-Di) | | | |
| Vinyl Chloride | 25.99 | 28.34 | 22.92 | 33.60 |
| Vinlyidene Chloride | 0.06 | 0.06 | 0.26 | 0.20 |
| Dichloroethylene Trans | 3.19 | 3.06 | 4.61 | 2.91 |
| Dichloroethylene Cis | 3.87 | 4.03 | 7.96 | 4.20 |
| 1,1,1-Trichloroethane | 0.02 | 0.01 | 0.002 | 0.02 |
| Trichloroethylene | 0.21 | 0.20 | 0.65 | 0.29 |
| 1,1,2-Trichloroethane | 62.81 | 60.83 | 59.95 | 56.52 |

*$R_T$ = residence time in seconds.

We claim:

1. A process for making 1,1,2-trichloroethane from 1,1-dichloroethane which comprises (1) mixing vapors of 1,1-dichloroethane with chlorine (2) reacting by passing said mixture over a Y-type molecular sieve (3) separating 1,1,2-trichloroethane from unreacted 1,1-dichloroethane and (4) recycling said 1,1-dichloroethane to the reaction.

2. The process of claim 1 wherein the temperature of reaction is from about 100° to about 350° C.

3. The process of claim 2 wherein the residence time is from about 0.1 to about 30 seconds.

4. The process of claim 3 wherein the residence time is from about 1 to about 3 seconds.

5. The process of claim 3 wherein the temperature of reaction is from about 110° to about 200° C.

6. The process of claim 3 wherein the molar ratio of chlorine to dichloroethane is from about 1:1 to about 1:10.

* * * * *